United States Patent [19]

Kosako et al.

[11] Patent Number: 5,317,605
[45] Date of Patent: May 31, 1994

[54] METHOD OF MEASURING REDUCTION OF SURFACE LAYER MATERIAL AND APPARATUS THEREFOR

[75] Inventors: Toshiso Kosako, Meguro; Kazuo Nishimura, Yokohama, both of Japan

[73] Assignee: General Sekiyu Kabushiki Kaisha, Japan

[21] Appl. No.: 19,336

[22] Filed: Feb. 18, 1993

Related U.S. Application Data

[63] Continuation of Ser. No. 488,977, Mar. 5, 1990, abandoned.

[30] Foreign Application Priority Data

Mar. 7, 1989 [JP] Japan .................................. 1-54770
Aug. 18, 1989 [JP] Japan ................................ 1-212181

[51] Int. Cl.$^5$ .............................................. G21G 1/10
[52] U.S. Cl. ..................................... 376/157; 376/159
[58] Field of Search .................................. 376/157, 159

[56] References Cited

U.S. PATENT DOCUMENTS

| | | | |
|---|---|---|---|
| 2,509,344 | 5/1950 | Herzog | 376/159 |
| 2,723,351 | 11/1955 | Garrison et al. | 376/159 |
| 2,751,506 | 6/1956 | Black et al. | 376/159 |
| 2,811,650 | 10/1957 | Wagner et al. | 376/159 |
| 2,967,937 | 1/1961 | McKay | 376/159 |
| 2,967,938 | 1/1961 | McKay et al. | 376/159 |
| 3,227,881 | 1/1966 | Gordon | 376/159 |
| 3,242,338 | 3/1966 | Danforth et al. | 376/159 |
| 3,315,076 | 4/1967 | Jordan | 376/159 |
| 3,898,459 | 8/1975 | Lechman et al. | 376/159 |
| 4,882,121 | 11/1989 | Grenier | 376/159 |
| 5,114,662 | 5/1990 | Gozani et al. | 376/159 |
| 5,153,439 | 10/1990 | Gozani et al. | 376/159 |

FOREIGN PATENT DOCUMENTS

2158941 11/1985 United Kingdom .

OTHER PUBLICATIONS

Tendera et al., *Radiochem Radioanal Letters*, 24(3) Feb. 1976 pp. 193–198.

Finnigan et al., *Corrosion Science*, vol. 22, No. 4, pp. 359–372.

Lambrev et al., *Radiochem Radioanal Letters*, 6(3), 1971, pp. 133–138.

S. J. S. Ryde et al., "A clinical instrument for multi-element in vivo analysis by prompt, delayed and cyclic neutron activation using 252Cf", Physics in Medicine and Biology, vol. 32, No. 10, Oct. 1987, pp. 1257–1271.

P. M. Read, "Erosion and transfer in electrical contacts measured using the thin layer activation technique". IEE Transactions on Components, Hybrids, and Manufacturing Technology, vol. CHMT-6, No. 2, Jun. 1983, pp. 218–221.

T. Kosako et al., "Wear measurements at depths of several tens micrometers on the surface of iron using a thin layer activation method by 7 Mev proton beam", 10th Int'l Conference on the Application of Accelerators in Research and Industry, Nov. 7–9, 1988, Denton, Tex.

INSPEC Database, Institute of Electrical Engineers, London, GB, Abstract No. A89096095.

(List continued on next page.)

*Primary Examiner*—Behrend E. Harvey
*Attorney, Agent, or Firm*—Wegner, Cantor, Mueller & Player

[57] ABSTRACT

A method in which a surface layer material whose amount of reduction is to be measured is activated to find a distribution ratio of two or more kinds of radioactive nuclides that are produced in the space in the surface layer of the material, and the distribution ratio is used as an index for the amount of reduction of surface layer material. The amount of reduction in the surface layer material is measured in situ, nondestructively, easily and irrespectively of obstacles and the distance that exist between the detector and the material that is to be measured.

3 Claims, 4 Drawing Sheets

OTHER PUBLICATIONS

T. Kosako and K. Nishimura, "Wear measurement at depth of several tens micrometers on the surface of iron using a thin layer activation method by 7 MeV proton beam", Nuclear Instruments and Methods in Physics Research, B40/41 (1989).

T. Kosako and K. Nishimura, "On-line and precise measurement of iron wear using thin layer activation reaction by proton beam". Procedures of the 2nd Int'l Symposium on Advanced Nuclear Energy Research—Evolution by Accelerators, Japan (1990) pp. 678–683.

T. W. Conlon, "Ion beam activation analysis for materials: methods and applications" IEE Transactions on Nuclear Science, vol. NS-28, No. 2, Apr. 1981.

World Patent Index Latest Database, Week 8533, Derwent Publications, Ltd., Class S03, No. 85-201744/33 & SU-A-1080605 (I. O. Konstantinov) Apr. 15, 1985.

Radiochem. Radioanal. Letters 24(3), (Feb. 1976), pp. 193–198, Tendera et al.

Corrosion Science, vol. 22, No. 4, (1982), pp. 359–372, Finnigan et al.

Radiochem. Radioanal. Letters 6(3), (1971) pp. 133–138, Lambrev et al.

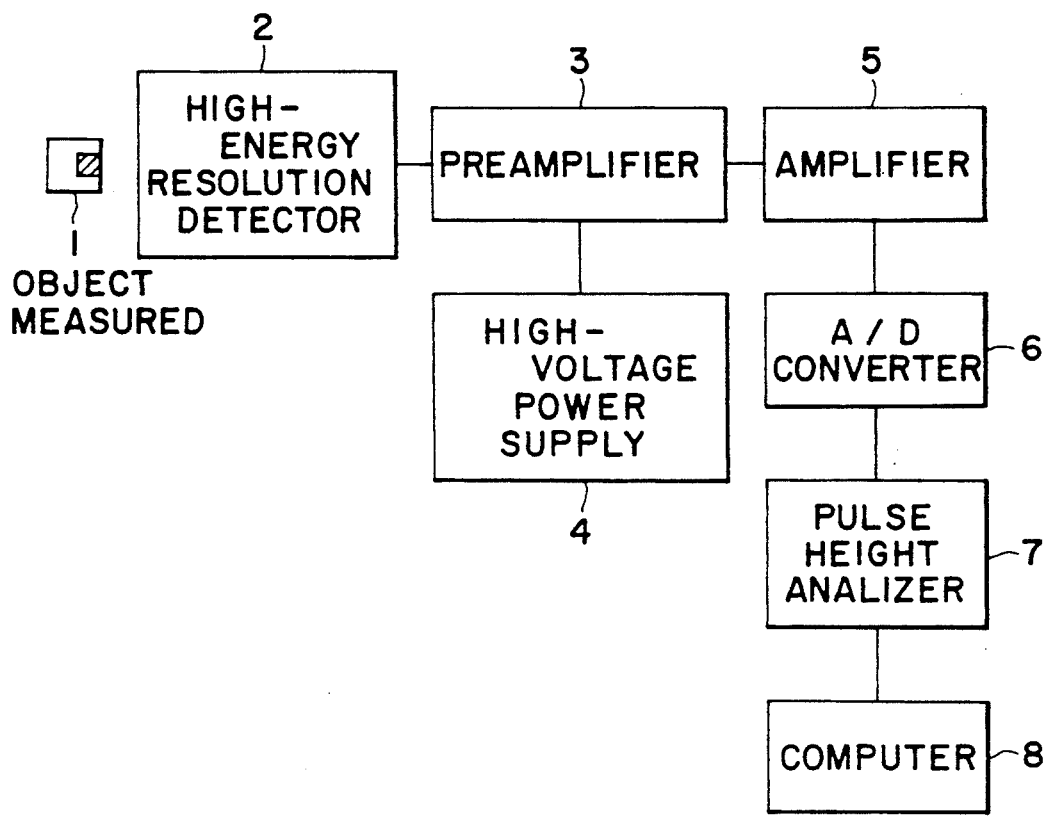
F I G. 1

METHOD OF MEASURING REDUCTION OF SURFACE LAYER MATERIAL AND APPARATUS THEREFOR

This application is a continuation of U.S. application Ser. No. 07/488,977 filed Mar. 5, 1990, now abandoned.

BACKGROUND OF THE INVENTION

1. Field of the Invention

The present invention relates to a method of measuring reduction of surface layer material and to an apparatus therefor. More specifically, the invention relates to a method of measuring reduction of surface layer material utilizing activation by neutrons and activation by charged particles and to an apparatus therefor.

2. Prior Art

Machinery and structures, made of various materials, in general, lose their surface layer materials with use because of action such as wear, corrosion, or erosion. A method of measuring such surface layer material reduction by utilizing activation by neutrons and activation by charged particles has heretofore been known. This method comprises essentially the following four steps.

First step (activation)—portions of two objects, which are a component to be actually measured and a reference calibration part, and which are made of the same material, are activated.

Second step (calibration)—a relationship is found for the reference calibration part between the radioactivity and the amount of reduction.

Third step (measurement)—radioactivity is measured for the component while the surface layer is being reduced gradually.

Fourth step (analysis)—the amount of reduction is found from the radioactivity measured in the third step and from the reference calibration obtained in the second step.

However, this method involves problems with regard to the following two points.

(1) Positional relationship between a detector and an object to be measured.

With reference to the above-mentioned third step (measurement), it was not so far possible to change the positional relationship between the detector and the object to be measured during the measurement. That is, the count rate and the amount of reduction could not be related to each other unless the intensity of gamma-rays was measured while maintaining the same positional relationship between the object to be measured and the detector. The intensity of gamma-rays at this positional relationship, was 100% at zero reduction on the calibration curve. This is because a change in the positional relationship between the detector and the object to be measured during the measurement results in a change in the counting efficiency of the detector. The counting efficiency of the detector is represented by the ratio of how much gamma-rays the detector detects out of the total gamma-rays emitted by the object that is to be measured. This varies depending upon how much gamma-rays reach the detector out of the total gamma-rays emitted by the object to be measured, but neglecting the specific response of the detector to the gamma-rays. That is, the counting efficiency for the gamma-rays decreases with the increase in the amount of obstacles and/or the distance that exist between the detector and the object to be detected, and the counting efficiency increases with the decrease in the amount of obstacles and/or the distance. As a result according to the conventional method, the count rate markedly decreases and error increases when the reduction of surface layer material proceeds and radioactivity remaining in the surface layer greatly decreases.

(2) Shape of beam

Charged particles travel in a straight path in a vacuum. Microscopically, however, their paths in a substance are not straight, the paths are bent due to interaction by the atomic nuclei, and the particles travel while losing their energy. When an irradiation field is great to some extent, a multi-bending path of the incident beam in the target substance does not matter much because cross sections of the activated region through the whole depth appear identical with a cross section of the incident beam. In practice, however, the edges swell outwardly beyond the circumference of the incident beam due to multi-bending of the path, but there is almost no effect on the calibration relationship since the swollen portion is very small compared with the irradiation field. When the beam has a very small cross section, on the other hand, the edge of the beam swells to a degree that can no longer be neglected with respect to the irradiation field. Even when the incident energy is the same, therefore, the calibration function varies depending upon the irradiation field, and the calibration operation must be carried out for each case.

SUMMARY OF THE INVENTION

An object of the present invention therefore is to provide a method of measuring reduction of surface layer material by utilizing activation reaction and permitting reduced amounts of error to take place using a generally applicable calibration function, thereby to solve the aforementioned problems inherent in the prior art.

The present invention therefore provides a method of measuring reduction of surface layer material wherein the reduction of surface layer material is substituted for a change in the radioactivity in the surface layer of the material activated by neutrons or charged particles to measure the residual radioactivity in the surface layer of the material or to measure the radioactivity of the material that is removed from the surface layer and is trapped by a filter, characterized in that a distribution ratio of two or more kinds of radioactive nuclides such as radioactive isotopes or different radioactive elements produced by the activation reaction is found in the space of the surface layer of said material and is used as an index for the reduction.

The present invention further provides an apparatus for measuring reduction of the surface layer material wherein the reduction of the surface layer material is substituted for a change in the radioactivity in the surface layer of the material activated by neutrons or charged particles to measure the residual radioactivity in the surface layer of the material or to measure the radioactivity of the material that is removed from the surface layer and is trapped by a filter, characterized in that provision is made of a device that measures the energy spectra of the radioactivity, and a device that analyzes said energy spectra for every two or more kinds of radioactive nuclides to find a ratio of spatial distributions thereof in order to find a calibration function and to measure the reduction of the surface layer material.

BRIEF DESCRIPTION OF THE DRAWINGS

FIG. 1 is a block diagram of a measuring system according to the present invention;

DESCRIPTION OF THE PREFERRED EMBODIMENT

An embodiment of the present invention will now be described in detail.

First Step (Activation)

Portions of two objects, which are a component to be actually measured and a reference calibration part, and which are made of the same material, are directly activated by neutrons or by charged particles, or an activated material is buried into said two objects. That is, the calibration part is used in a second step for calibration, and the component is used in a third step to measure the radioactivity in order to find the surface layer reduction from the calibration function. Here, the surface layer having the same activated spatial distribution is reproduced by setting the activation conditions to be the same, i.e., by setting the kind of neutrons or charged particles, the beam energy, the irradiation field, and the target material to be the same.

The following activation reactions take place when the surface of a cast iron block (Fe, 95%) cut from the cam shaft of an automotive engine and a cam nose of the cam shaft are irradiated with a proton beam of 7 MeV using, for example, a Tandem Van de Graaff accelerator. $^{56}Fe\ (p, n)^{56}Co\ ^{57}Fe\ (p, n)^{57}Co\ ^{58}Fe\ (p, n)^{58}Co$ In this case, three kinds of radioactive nuclides are produced at the same time and are distributed within about 100 $\mu$m in the surface layer of the material. For instance, $^{56}Co$ is formed only up to a depth of 50 $\mu$m, but $^{57}Co$ and $^{58}Co$ are formed up to depths of a hundred and several tens of micrometers; i.e., activated radioactive spatial distributions are different among these radioactive nuclides. An important feature of the present invention resides in paying attention to the difference in the radioactive spatial distributions for every two or more kinds of radioactive nuclides.

Second Step (Calibration)

The calibration part activated in the first step is simulated for its practical phenomenon of surface layer reduction by using a polisher. At the same time, the reduction is precisely measured in terms of a unit of mass or length, and further, the intensity of gamma-rays is precisely measured as residual radioactivity in the surface layer or as radioactivity of debris removed from the surface layer. The ratios of radioactivity are found among the radioactive nuclides at each of the depths of reduction to find a calibration function.

Figure 2:
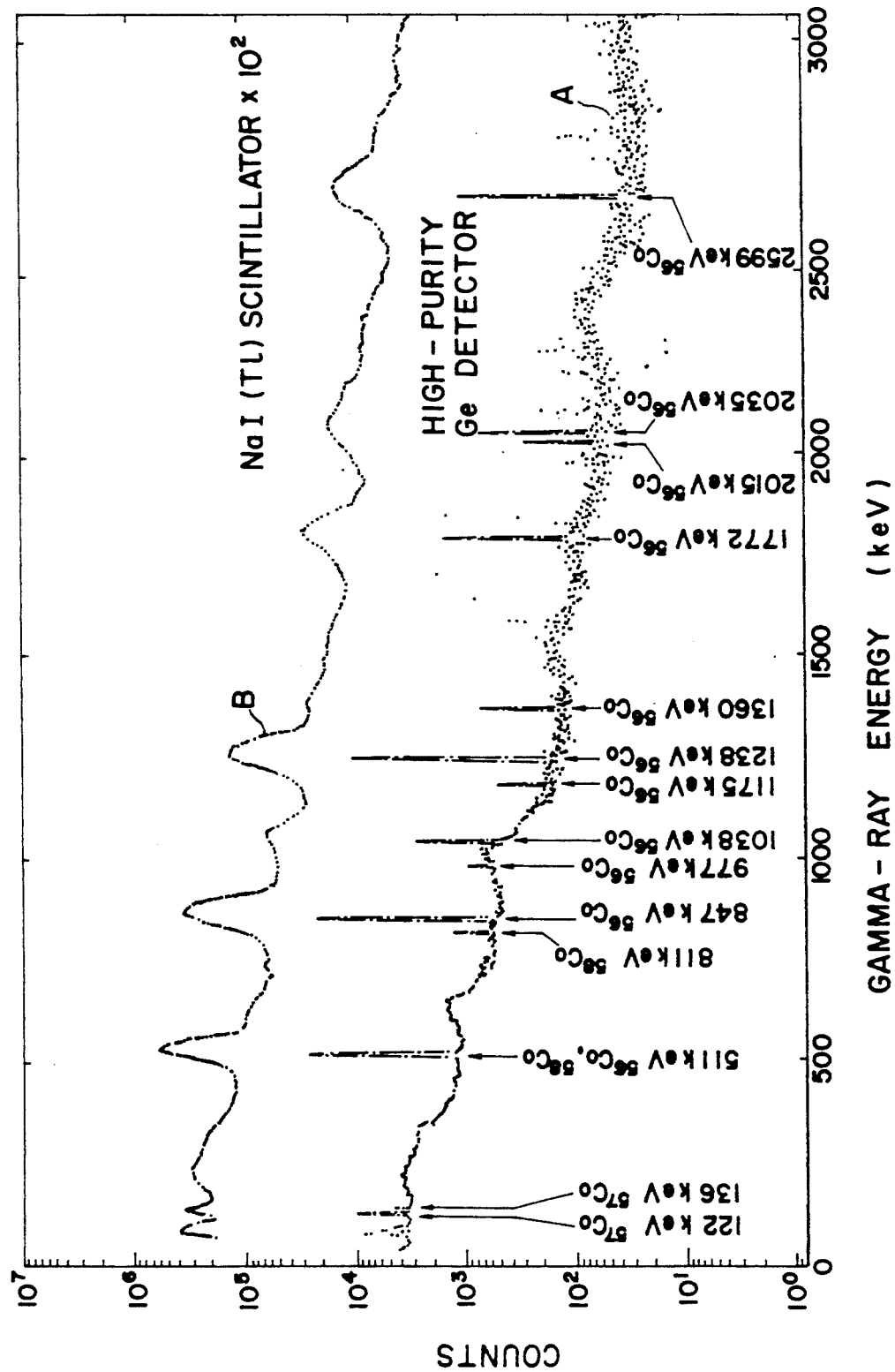
FIG. 2 is a graph of gamma-ray energy spectra of radioactive nuclides that are produced when a cast iron block is irradiated with protons of 7 MeV according to an embodiment of the present invention.

FIG. 2 shows an energy spectrum A of radioactivity when the cast iron block whose surface layer is activated in the first step is measured for its gamma-rays using a high energy resolution detector such as a high-purity germanium detector. FIG. 2 also shows a gamma-ray spectrum B of an NaI(Tl) scintillator which cannot usually separate neighboring gamma-ray energy peaks. It will be found that 811 keV of $^{58}Co$ and 847 keV of $^{56}Co$ that are not separated by the NaI(Te) scintillator are well separated by the high-purity germanium detector that has a high energy resolution. Radioactivities of the produced radioactive nuclides are determined from the measurement of the spectra, and the ratios of spatial distributions are found for the nuclides.

After the produced radioactivities are determined, the practical phenomenon of surface layer reduction of the cast iron block is simulated using a polisher. The cast iron block is stepwisely polished by about 1 $\mu$m each time. At the same time, the reduction of thickness is precisely measured in the activated region using a micrometer, and the residual radioactivity in the surface layer is measured by the aforementioned method to find ratios for nuclides.

Figure 3:
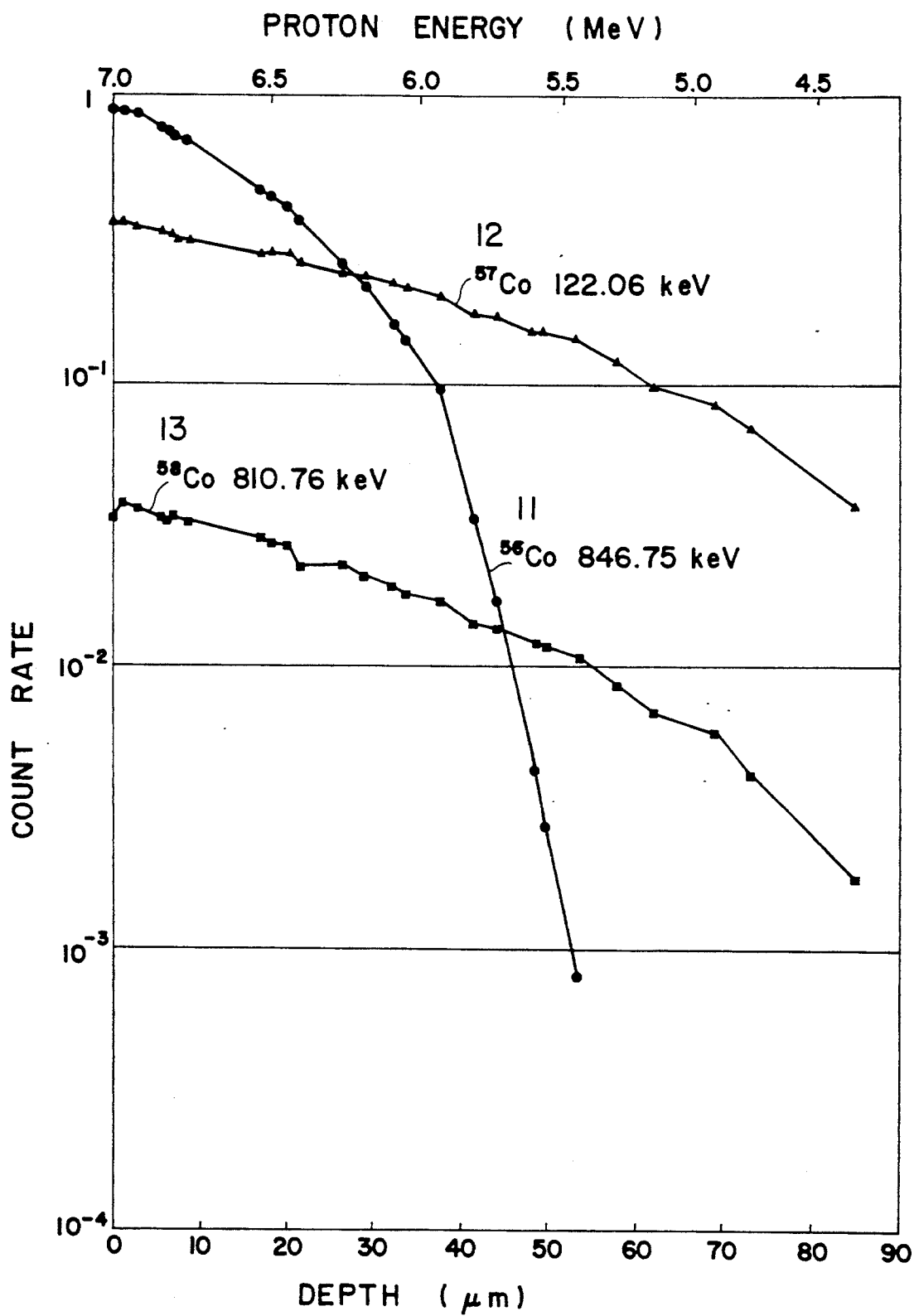
FIG. 3 is a graph showing relationships of the depth of reduction and the residual radioactivity of the produced nuclides found by using a high-purity germanium detector.

FIG. 3 is a graph in which the residual radioactivities are plotted for every radioactive nuclide for each depth. When measurement is performed not using a high-purity germanium detector but a NaI(Tl) scintillator, the gamma-ray peaks of 847 keV of $^{56}Co$ and 811 keV of $^{58}Co$ are not separated, and there is obtained a complex curve in which curves 11 and 13 are combined. Further, low-energy gamma-rays such as 122 key of $^{57}Co$ are difficult to determine because of bad resolution in such a low energy region and from which no curve is obtained. According to the present invention, therefore, it is necessary to use a detector of a high energy resolution such as a high-purity germanium detector.

Thus, calibration relationships are examined between the reduction of thickness and the radioactivities for each nuclide of the sample, and are analyzed through a computer in order to find radioactivity ratios in spatial distributions, as a calibration function, i.e., radioactivity ratios of $^{56}Co/^{57}Co$, $^{56}Co/^{58}Co$. By adapting the ratio of spatial distributions shown in FIG. 4 to the calibration function, it is possible to easily find the depth of surface layer reduction or the amount of surface layer reduction from this new relationship.

According to the present invention as described above, the spatial distributions are found for various radioactive nuclides, and ratios of spatial distributions of radioactive nuclides such as $^{56}Co/^{57}Co$, $^{56}Co/^{58}Co$ are corresponded to the amounts of surface layer reduction to obtain a curve of calibration. The ratios are used as a calibration function for measuring the amount of surface layer reduction, i.e., as an index for the amount of reduction.

Third and Fourth Step (Measurement and Analysis)

The component, which has been activated in the first step, is placed in the environment in which the component suffers surface layer reduction by wear, corrosion, or erosion, then the radioactivity of the component is measured. For instance, when it is desired to measure the amount of wear in the cam nose of the automotive engine, the cam nose is activated by the irradiation with a proton beam of 7 MeV and is then installed in the engine. Here, if the calibration relation is found according to the present invention as mentioned earlier, the particles for activation must have the same energy as that of when the calibration relation was found irrespective of the irradiation field. At the early stage of measurement, a long distance should be maintained between the detector and the cam nose, because the count rate of gamma-rays is great, and the detector has an increased dead time before the wear takes place. Because the count rate of gamma-rays decreases as the wear increases, the distance should be decreased between the detector and the cam nose in order to increase the count rate and to decrease error.

As described above, the residual radioactivity of the engine cam nose after the surface layer reduction is measured for every radioactive nuclide, and ratios are found between the radioactive nuclides.

Figure 4:
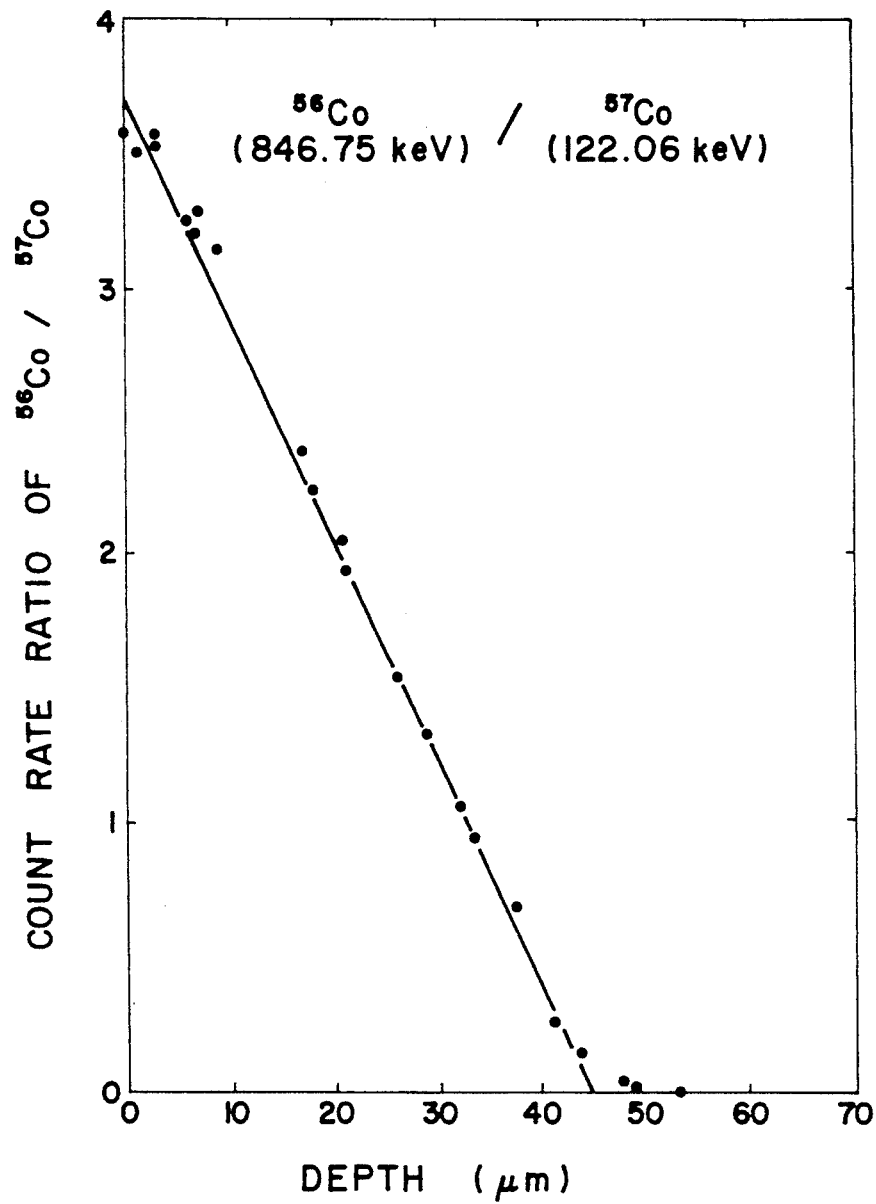
FIG. 4 is a graph showing a relationship of the amount (depth) of reduction and the ratio of nuclides found by using the above detector.

A ratio between radioactive nuclides after the surface layer reduction is found, e.g., a ratio $^{56}Co/^{57}Co$ is found and is applied to the graph of FIG. 4 that is obtained in the second step. From this ratio, therefore, the depth of surface layer reduction is easily found, i.e., the amount of surface layer reduction is easily found. According to the present invention as described above, the amount of wear in, for example, the engine cam nose can be found easily and precisely by measuring the energy spectra of residual radioactivity in situ, nondestructively, and in real time.

FIG. 1 is a block diagram of the measuring system according to the present invention, wherein reference numeral 1 denotes an object that is to be measured of which the surface layer has been activated, 2 denotes a high energy resolution detector such as a high-purity germanium detector, 3 denotes a preamplifier, 4 denotes a high-voltage power supply, 5 denotes an amplifier, 6 denotes an analog-to-digital converter, 7 denotes a pulse height analyzer, and 8 denotes a computer.

In this system, first, the energy spectra of radioactivity are found by the detector 2. The computer 8 has the functions of a calculation unit which analyzes the energy spectra for every radioactive nuclide, a memory which stores them as radioactive spatial distribution for every radioactive nuclide, a calculation unit which finds, as a calibration function of surface layer reduction, a ratio of activated spatial distributions for every radioactive nuclide sent from the memory, a memory which stores the calibration function of the amount of surface layer reduction found by the calculation unit, and a calculation unit which finds ratios for the radioactive nuclides from the measured energy spectra of gamma-rays and converts them into amounts of surface layer reduction.

According to the present invention as described above, the surface layer of a material is activated to find a distribution ratio of two or more radioactive nuclides produced by activation reactions, and this ratio is used as a calibration relationship for measuring the amount of surface layer reduction of the material or as an index of the amount of surface layer reduction. Since the radioactivity ratio among the nuclides is used, this relationship serves as a dimensionless and generally applicable calibration relationship which is not dependent upon the counting efficiency of energies as long as the detector has a detection efficiency which is little dependent upon the energy. Therefore, if once this function is found, the amount of reduction can be easily found irrespective of the positional relationship between the detector and the object to be measured, obstacles between them such as casing of the device or the air and so forth, or the irradiation field.

In the foregoing was described the case where the residual radioactivity was to be measured in the surface layer of the material by the activation with charged particles. The present invention can also be put into practice in the same manner by measuring the radioactivity of the material removed from the surface layer and trapped by a filter, and can further be put into practice by using radioactive isotopes and radioactive elements of different nuclides even in the case of activation with neutrons or even when the activation with neutrons and the activation with charged particles are combined. Furthermore, not only wear but also any phenomena of surface layer reduction in the general machinery and structures caused by wear, corrosion and erosion as they are used, can be measured in situ, nondestructively, and in real time. The present invention can be applied not only to metallic materials but also to such materials as ceramics and plastics.

According to the present invention as described above, attention is given to differences in the activated spatial distributions of the radioactive nuclides, and a ratio of activated spatial distributions of the radioactive nuclides is used as a new calibration relationship to take measurement irrespective of the amount of obstacles and the distance that exist between the detector and the object that is to be measured. The distance is shortened between the detector and the object that is to be measured with the decrease in the count rate as the thickness is reduced, whereby the count rate is increased to decrease error. By using the above ratio as a new calibration relationship, the swell at the end of the beam can be neglected, and a calibration relationship is obtained irrespective of the irradiation field.

As described above, the present invention provides a method and an apparatus that are capable of effectively measuring the amounts of reduction in the surface layer material of an object.

What is claimed is:

1. A method of measuring the reduction of surface layer material of a test object by comparison with a reference object made of the same material as the test object comprising the steps of:
   (a) activating the surface layer material of the reference object with charged particles to cause an activation reaction so as to produce different ratios of at least two radioactive nuclides produced by the activation reaction at different depths;
   (b) subsequently removing a predetermined thickness of the surface layer material of said reference object to produce a reduced surface layer;
   (c) measuring the radioactivity caused by the activation reaction in the initial surface layer material and in the reduced surface layer material of the reference object using a high energy resolution detector;
   (d) determining a distribution ratio of the at least two radioactive nuclides produced by the activation reaction in the reference object;
   (e) repeating steps (a) to (d) a sufficient number of times to establish a relationship which can be used to relate the reduction of the surface layer material with a change in the radioactivity in the surface layer material;
   (f) activating the surface layer material of the test object with a beam of charged particles identical to that used with said reference objects to cause an activation reaction;
   (g) measuring the radioactivity caused by the activation reaction in the surface layer material of the test object using a high energy resolution detector after the test object has been subjected to wear over a predetermined period of time;

(h) determining a distribution ration of the at least two radioactive nuclides produced by the activation reaction in the test object; and (i) calculating any reduction in the surface layer material of the test object due to wear based on the relationship between the ratio of the at least two radioactive nuclides and the reduction in the surface layer which was established for said reference object.

2. A method of measuring reduction of the surface layer material according to claim 1, wherein said radioactive nuclides are $^{56}$Co, $^{57}$Co and $^{58}$Co, said charged particles are protons, and said surface layer material is iron.

3. A method of measuring reduction of the surface layer material according to claim 1, wherein said high energy resolution detector is a high-purity germanium detector.

* * * * *